United States Patent [19]
Bär et al.

[11] Patent Number: 6,043,263
[45] Date of Patent: Mar. 28, 2000

[54] (2,3-DIHYDROBENZOFURANYL)-THIAZOLES AS PHOSPHODIESTERASE INHIBITORS

[75] Inventors: Thomas Bär; Wolf-Rüdiger Ulrich, both of Constance, Germany

[73] Assignee: Byk Gulden Lomberg Chemische Fabrik GmbH, Constance, Germany

[21] Appl. No.: 09/284,989

[22] PCT Filed: Nov. 5, 1997

[86] PCT No.: PCT/EP97/06131

§ 371 Date: May 22, 1999

§ 102(e) Date: May 22, 1999

[87] PCT Pub. No.: WO98/21207

PCT Pub. Date: May 22, 1998

[30] Foreign Application Priority Data

Nov. 12, 1996 [DE] Germany ............................ 196 46 503
Nov. 16, 1996 [EP] European Pat. Off. .............. 96118414

[51] Int. Cl.$^7$ ........................ C07D 417/04; A61K 31/425
[52] U.S. Cl. ........................ 514/365; 514/337; 546/269; 548/203; 548/204
[58] Field of Search .................... 548/203, 204; 546/269; 514/365, 337

[56] References Cited

U.S. PATENT DOCUMENTS 5,639,770  6/1997  Chihiro ............................ 514/365
5,677,319  10/1997  Chihiro ............................ 514/365
5,814,651  9/1998  Duplantier ......................... 514/394

*Primary Examiner*—Robert Gerstl
*Attorney, Agent, or Firm*—Jacobson, Price, Holman & Stern, PLLC

[57] ABSTRACT

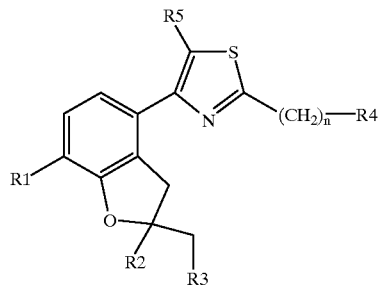

(I)

The invention relates to compounds of the formula (I), wherein R1, R2, R3, R4, R5 and n have the meanings cited in the description said compounds being new effective bronchial therapeutic agents.

9 Claims, 2 Drawing Sheets

FORMULA SHEET I
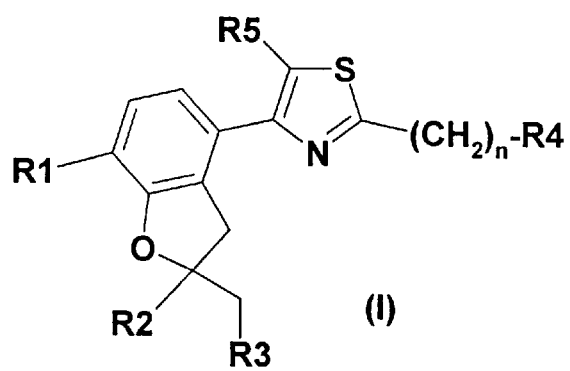
(I)
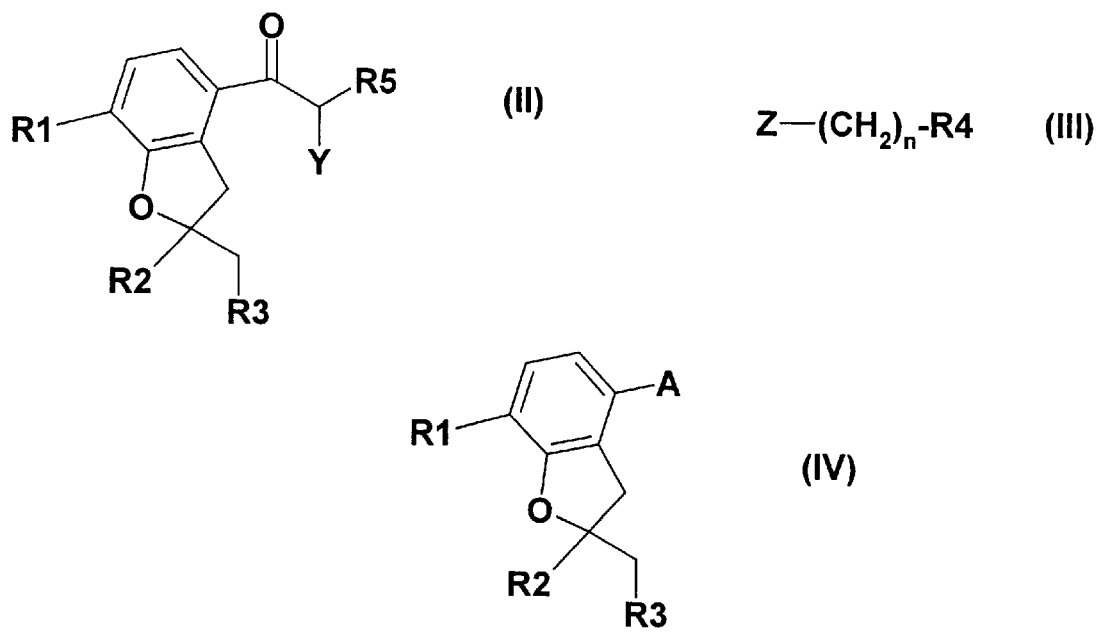

FORMULA SHEET II
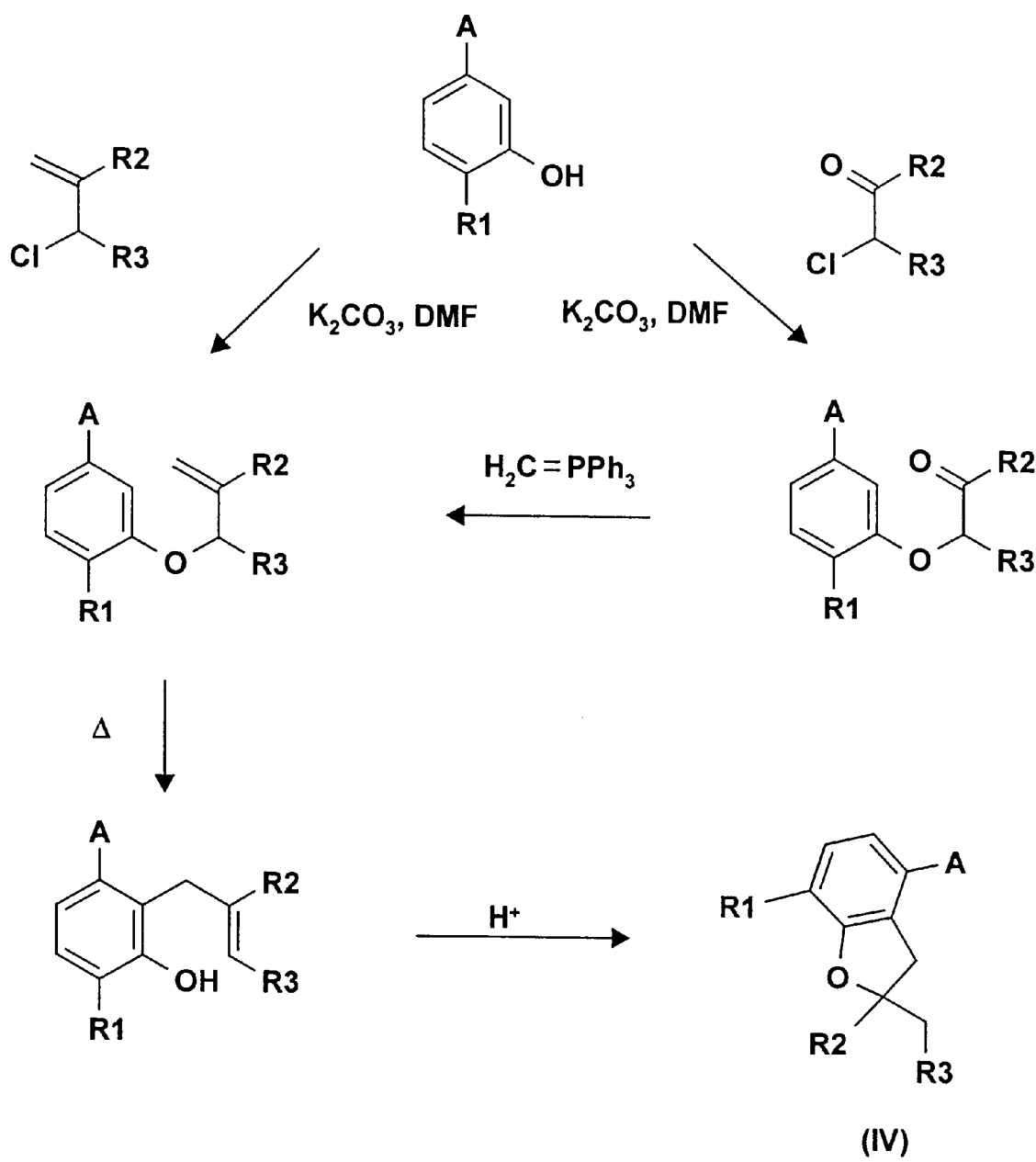
(IV)

(2,3-DIHYDROBENZOFURANYL)-THIAZOLES AS PHOSPHODIESTERASE INHIBITORS

FIELD OF APPLICATION OF THE INVENTION

The invention relates to novel thiazole derivatives which are used in the pharmaceutical industry for the production of medicaments.

KNOWN TECHNICAL BACKGROUND

Japanese patent specification JP 46-15935 describes substituted 4-(carboxyphenyl)thiazoles and their use for the treatment of thrombosis, arteriosclerosis, gastric ulcers and hypersecretion. European patent applications EP 0 513 387 and EP 0 600 092 describe, inter alia, 4-(substituted phenyl) thiazole derivatives, 4-(substituted 2,3-dihydrobenzofuran) thiazole derivatives and their use as inhibitors of oxygen radical release by neutrophils. The compounds are therefore described as suitable for the treatment of acute inflammatory processes such as ischemia and reperfusion damage.

International patent application WO94/12461 describes 4-substituted catechol diethers, which are substituted in the 4-position, inter alia, with thiazole derivatives, and their use as inhibitors of phosphodiesterase IV.

DESCRIPTION OF THE INVENTION

It has now surprisingly been found that the novel thiazole derivatives described below in greater detail, which differ from the previously published thiazoles, in particular, by the substituents on the 4-(2,3-dihydrobenzofuran ring), are selective inhibitors of phosphodiesterase IV.

The invention thus relates to compounds of the formula I (see attached formula sheet I), in which R1 is hydroxyl, 1–4C-alkoxy, 3–7C-cycloalkoxy, 3–7C-cycloalkylmethoxy, benzyloxy or 1–4C-alkoxy which is completely or mainly substituted by fluorine, R2 is hydrogen or 1–4C-alkyl and R3 is hydrogen or 1–4C-alkyl, or R2 and R3, together and including the two carbon atoms to which they are bonded, are a 5-, 6- or 7-membered hydrocarbon ring which, if desired, is interrupted by an oxygen atom, R4 is a phenyl or naphthyl ring which is substituted by R41, R42 and R43, a mono- or bicyclic heterocycle which is substituted by R44, R45 and R46 and which is selected from the group consisting of pyridine, pyrrole, quinoline, isoquinoline, indole, isoindole, indolizine, pyrimidine, pyrazine, pyridazine, quinoxaline, quinazoline, cinnoline, benzimidazole, thiophene and furan or a mono- or bicyclic heterocycle which is substituted by R44 and R45 and which is selected from the group consisting of pyrazole, imidazole, purine, oxazole, isoxazole, thiazole and isothiazole, where R41 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylami-nosulfonyl, amino, mono- or di-1–4C-alkylamino, 1–4C-alkylcarbonylamino, 1–4C-alkylsulfonyl, 1–4C-alkoxysulfonyl, hydroxy-1–4C-alkyl, hydroxyl, 1–4C-alkoxy, 1–4C-alkyl, 1–4C-alkylcarbonyl, 1–4C-alkylcarbonyloxy, halogen, cyano or nitro, R42 is hydrogen, 1–4C-alkoxy which is completely or mainly substituted by fluorine, hydroxyl, amino, nitro, halogen, 1–4C-alkoxycarbonyl, 1–4C-alkylcarbonyloxy, 1–4C-alkylcarbonyl, carboxyl, 1–4C-alkyl or 1–4C-alkoxy, R43 is hydrogen, 1–4C-alkoxy, halogen or hydroxyl, R44 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, hydroxy-1–4C-alkyl, hydroxyl, 1–4C-alkoxy, 1–4C-alkyl, 1–4C-alkylcarbonyl, 1–4C-alkylcarbonyloxy, halogen, cyano or nitro, R45 is hydrogen, hydroxyl, halogen, carboxyl, amino, 1–4C-alkyl, 1–4C-alkylcarbonyl, 1–4C-alkoxycarbonyl or 1–4C-alkoxy and R46 is hydrogen, halogen, 1–4C-alkoxy or 1–4C-alkyl, R5 is hydrogen or halogen, n is 0, 1 or 2, the salts of these compounds and the N-oxides of the pyridines, quinolines, isoquinolines, pyrimidines, pyrazines, imidazoles, quinoxalines, quinazolines and benzimidazoles and their salts.

1–4C-alkyl represents straight-chain or branched alkyl radicals having 1 to 4 carbon atoms. Examples which may be mentioned are the butyl, the isobutyl, the secbutyl, the tert-butyl, the propyl, the isopropyl, the ethyl and the methyl radical.

1–4C-alkoxy represents a radical which, in addition to the oxygen atom, contains one of the abovementioned straight-chain or branched alkyl radicals having 1 to 4 carbon atoms. Alkoxy radicals having 1 to 4 carbon atoms which may be mentioned here are, for example, the butoxy, isobutoxy, sec-butoxy, tert-butoxy, propoxy, isopropoxy, ethoxy and the methoxy radical.

3–7C-cycloalkoxy represents the cyclopropyloxy, cyclobutyloxy, cyclopentyloxy, cyclohexyloxy and cycloheptyloxy radical. The 3–5C-cycloalkoxy radicals cyclopropyloxy, cyclobutyloxy and cyclopentyloxy may preferably be mentioned.

3–7C-cycloalkylmethoxy represents cyclopropylmethoxy, cyclobutylmethoxy, cyclopentylmethoxy, cyclohexylmethoxy and cycloheptylmethoxy. The 3–5C-cycloalkylmethoxy radicals cyclopropylmethoxy, cyclobutylmethoxy and cyclopentylmethoxy may preferably be mentioned.

1–4C-alkoxy completely or mainly substituted by fluorine which may be mentioned is, for example, the 1,2,2-trifluoroethoxy, the 2,2,3,3,3-pentafluoroethoxy, the perfluoroethoxy and in particular the 1,1,2,2-tetrafluoroethoxy, the trifluoromethoxy, the 2,2,2-trifluoroethoxy and preferably the difluoromethoxy radical.

A 5-, 6- or 7-membered hydrocarbon ring, if desired interrupted by an oxygen atom, which may be mentioned is the cyclopentane, the cyclohexane, the cycloheptane, the tetrahydrofuran and the tetrahydropyran ring. If R2 and R3, together and including the two carbon atoms to which they are bonded, form a 5-, 6- or 7-membered ring, a spiro compound is present.

Halogen within the meaning of the invention is fluorine, chlorine, bromine and iodine, fluorine, chlorine and bromine being preferred.

Mono- or di-1–4C-alkylamino radicals which may be mentioned are, for example, the methylamino, the dimethylamino, the ethylamino, the diethylamino, the propylamino and the isopropylamino radical.

Mono- or di-1–4C-alkylaminocarbonyl represents a carbonyl group to which one of the abovementioned mono- or di-1–4C-alkylamino radicals is bonded. Examples which may be mentioned are the methylaminocarbonyl, the dimethylaminocarbonyl and the ethylaminocarbonyl radical.

Mono- or di-1–4C-alkylaminosulfonyl represents a sulfonyl group to which one of the abovementioned mono- or di-1–4C-alkylamino radicals is bonded. Examples which may be mentioned are the methylaminosulfonyl, the di-methylaminosulfonyl and the ethylaminosulfonyl radical.

A 1–4C-alkylaminocarbonyl radical which may be mentioned, for example, is the acetylamino radical (—NH—CO—CH$_3$).

1–4C-alkoxycarbonyl represents a carbonyl group to which one of the abovementioned 1–4C-alkoxy radicals is bonded. Examples which may be mentioned are the methoxycarbonyl radical (CH$_3$O—CO—) and the ethoxycarbonyl radical (CH$_3$CH$_2$O—CO—).

1–4C-alkylcarbonyl represents a carbonyl group to which one of the abovementioned 1–4C-alkyl radicals is bonded. An example which may be mentioned is the acetyl radical (CH$_3$CO—).

In addition to the oxygen atom, 1–4C-alkylcarbonyloxy radicals contain a 1–4C-alkylcarbonyl radical. An example which may be mentioned is the acetoxy radical (CH$_3$CO—O—).

Hydroxy-1–4C-alkyl represents abovementioned 1–4C-alkyl radicals which are substituted by a hydroxyl group. Examples which may be mentioned are the hydroxyethyl and the hydroxymethyl radical.

1–4C-alkylsulfonyl represents a sulfonyl group to which one of the abovementioned 1–4C-alkyl radicals is bonded. An example which may be mentioned is the methylsulfonyl radical (CH$_3$SO$_2$—).

1–4C-alkoxysulfonyl represents a sulfonyl group to which one of the abovementioned 1–4C-alkoxy radicals is bonded. Examples which may be mentioned are the methoxysulfonyl radical (CH$_3$O—SO$_2$—) and the ethoxysulfonyl radical (CH$_3$CH$_2$O—SO$_2$—).

The linkage of the substituent R4 to the radical of the compounds of the formula I can take place via any suitable ring position of the phenyl or naphthyl ring or of the heterocycle, the linkage of the heterocycles not taking place via a ring heteroatom.

As examples of R4, the radicals phenyl, 3,4-dihydroxyphenyl, 3,4-dimethoxyphenyl, 3,4,5-trimethoxyphenyl, 3,5-dimethoxyphenyl, 2,3-dimethoxyphenyl, 2,4-dimethoxyphenyl, 3-methoxy-4-hydroxyphenyl, 3-hydroxy-4-methoxyphenyl, 4-methoxyphenyl, 4-chlorophenyl, 4-ethoxycarbonylphenyl, 3,4-diethoxyphenyl, 3,4-dimethylphenyl, 4-fluorophenyl, 3-chloro-4-methylphenyl, 3-nitrophenyl, 3,4-dichlorophenyl, 4-bromophenyl, 3,4-dibutoxyphenyl, 3,4-dipropoxyphenyl, 3-ethoxy-4-methoxyphenyl, 3-bromo-4,5-dimethoxyphenyl, 3,4-diacetoxyphenyl, 4-dimethylaminophenyl, 3-methoxy-4-methylsulfonylphenyl, 3-methoxycarbonyl-4-hydroxyphenyl, 4-acetamido-3-fluorophenyl, 4-acetamidophenyl, 4-acetamidonaphthyl, 4-acetamido-3-trifluoromethoxyphenyl, 3-acetylphenyl, 4-acetylphenyl, 2-carbamoylphenyl, 3-carbamoylphenyl, 4-carbamoylphenyl, 2-carboxy-4-methoxyphenyl, 3-carboxyphenyl, 4-carboxyphenyl, 3-methoxycarbonylphenyl, 5-indolyl, 4-nitrophenyl, 4-sulfonamidophenyl, 4-sulfophenyl, pyrimidin-2-yl, thiophen-3-yl, thiophen-2-yl, pyrrol-2-yl, 2-hydroxypyridin-3-yl, (pyridin-N-oxide)-3-yl, 5-acetyl-2-hydroxy-6-methylpyrid-3-yl, 5-acetyl-2,4-di-methylpyrid-3-yl, 2-chloro-pyrid-3-yl, 2-chloropyrid-4-yl, 2-chloropyrazin-3-yl, quinolin-3-yl, 2,6-dihydroxy-4-methylpyrid-3-yl, 4-nitropyrid-2-yl, purin-6-yl, 2-carboxypyrid-4-yl, 2-ethoxycarbonylpyrid-4-yl, 6-methylpyrid-2-yl, pyrazin-2-yl, 2-pyridyl, 3-pyridyl and 4-pyridyl may be mentioned.

Suitable salts of compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether it is a mono- or polybasic acid and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too in salt preparation, the bases are employed in an equimolar quantitative ratio or one differing therefrom.

Pharmacologically intolerable salts, which can be initially obtained as process products, for example, in the preparation of the compounds according to the invention on an industrial scale, are converted into pharmacologically tolerable salts by processes known to the person skilled in the art.

Compounds of the formula I to be emphasized are those in which

R1 is 1–4C-alkoxy, 3–5C-cycloalkoxy, 3–5C-cycloalkylmethoxy or 1–4C-alkoxy which is completely or mainly substituted by fluorine, R2 is 1–4C-alkyl and R3 is hydrogen or 1–4C-alkyl, or R2 and R3, together and including the two carbon atoms to which they are bonded, are a cyclopentane, cyclohexane, tetrahydrofuran or tetrahydropyran ring, R4 is a phenyl ring which is substituted by R41 and R42 or a mono- or bicyclic heterocycle which is substituted by R44 and R45 and which is selected from the group consisting of pyridine, pyrrole, quinoline, isoquinoline, indole, isoindole, indolizine, pyrimidine, pyrazine, pyridazine, pyrazole, imidazole, quinoxaline, quinazoline, cinnoline, benzimidazole, oxazole, isoxazole, thiazole and isothiazole, where R41 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, 1–4C-alkylsulfonyl, 1–4C-alkoxysulfonyl, hydroxy-1–4C-alkyl, hydroxyl, 1–4C-alkoxy, 1–4C-alkyl, 1–4C-alkylcarbonyl, 1–4C-alkylcarbonyloxy, halogen, cyano or nitro, R42 is hydrogen, hydroxyl, nitro, halogen, 1–4C-alkoxycarbonyl, 1–4C-alkylcarbonyloxy, 1–4C-alkylcarbonyl, carboxyl, or 1–4C-alkoxy, R44 is hydrogen, carboxyl, 1–4C-alkoxycarbonyl, carbamoyl, hydroxysulfonyl, sulfamoyl, mono- or di-1–4C- alkylaminocarbonyl, mono- or di-1–4C-alkylaminosulfonyl, amino, mono- or di-1–4C-alkylamino, 1–4C-alkylcarbonylamino, hydroxy-1–4C-alkyl, hydroxyl, 1–4C-alkoxy, 1–4C-alkyl, 1–4C-alkylcarbonyl, halogen or cyano and R45 is hydrogen, hydroxyl, halogen, carboxyl, amino, 1–4C-alkyl, or 1–4C-alkoxy, R5 is hydrogen or halogen, n is 0 or 1, the salts of these compounds and the N-oxides of the pyridines, quinolines, isoquinolines, pyrimidines, imidazoles, quinoxalines, quinazolines and benzimidazoles and their salts.

Compounds of the formula I particularly to be emphasized are those in which

R1 is 1–4C-alkoxy, 3–5C-cycloalkoxy or 1–2C-alkoxy which is completely or mainly substituted by fluorine, R2 and R3, together and including the two carbon atoms to which they are bonded, are a cyclopentane or cyclohexane ring, R4 is a phenyl ring which is substituted by R41 and R42 or a mono- or bicyclic heterocycle which is substituted by R44 and R45 and which is selected from the group consisting of pyridine, pyrrole, quinoline, isoquinoline, indole, isoindole, indolizine and pyrazine, where R41 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, 1–4C-alkylsulfonyl, 1–4C-alkoxysulfonyl, hydroxy-1–4C-alkyl, hydroxyl, 1–4C-alkoxy, 1–4C-alkyl, 1–4C-alkylcarbonyl, 1–4C-alkylcarbonyloxy, halogen, cyano or nitro, R42 is hydrogen, hydroxyl, nitro, halogen, 1–4C-alkoxycarbonyl, 1–4C-alkylcarbonyloxy, 1–4C-alkylcarbonyl, carboxyl or 1–4C-alkoxy, R44 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, hydroxy-1–4C-alkyl, hydroxyl, 1–4C-alkoxy, 1–4C-alkyl, 1–4C-alkylcarbonyl, halogen or cyano and R45 is hydrogen, hydroxyl, halogen, carboxyl, amino, 1–4C-alkyl or 1–4C-alkoxy, R5 is hydrogen, n is 0, the salts of these compounds and the N-oxides of the pyridines, quinolines and isoquinolines and their salts.

Preferred compounds of the formula I are those in which

R1 is 1–4C-alkoxy or 1–2C-alkoxy which is completely or mainly substituted by fluorine, R2 and R3, together and including the two carbon atoms to which they are bonded, are a cyclopentane ring, R4 is a phenyl ring which is substituted by R41 and R42 or pyridine or pyrazine which is substituted by R44 and R45, where R41 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, 1–4C-alkylsulfonyl, 1–4C-alkoxysulfonyl, hydroxy-1–4C-alkyl, hydroxyl, 1–4C-alkoxy, 1–4C-alkyl, 1–4C-alkylcarbonyl, 1–4C-alkylcarbonyloxy, halogen, cyano or nitro, R42 is hydrogen, hydroxyl, nitro, halogen, 1–4C-alkoxycarbonyl, 1–4C-alkylcarbonyloxy, 1–4C-alkylcarbonyl, carboxyl or 1–4C-alkoxy, R44 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, hydroxy-1–4C-alkyl, hydroxyl, 1–4C-alkoxy, 1–4C-alkyl, 1–4C-alkylcarbonyl, halogen or cyano and R45 is hydrogen, hydroxyl, halogen, carboxyl, amino, 1–4C-alkyl or 1–4C-alkoxy, R5 is hydrogen, n is 0, the salts of these compounds and the N-oxides of the pyridines and their salts.

Particularly preferred compounds of the formula I are those in which

R1 is 1–4C-alkoxy,

R2 and R3, together and including the two carbon atoms to which they are bonded, are a cyclopentane ring, R4 is a phenyl ring which is substituted by R41 or pyridine which is substituted by R44, where R41 is hydrogen, carboxyl, 1–4C-alkoxycarbonyl, carbamoyl, hydroxysulfonyl, sulfamoyl or hydroxyl and R44 is hydrogen, carboxyl, 1–4C-alkoxycarbonyl, carbamoyl, hydroxysulfonyl, sulfamoyl or hydroxyl, R5 is hydrogen, n is 0 and the salts of these compounds.

Particularly preferred compounds of the formula I to be emphasized are those in which R1 is methoxy, R2 and R3, together and including the two carbon atoms to which they are bonded, are a cyclopentane ring, R4 is a phenyl ring which is substituted by R41 or pyridine which is substituted by R44, where R41 is carboxyl and R44 is hydrogen, carboxyl or 1–4C-alkoxycarbonyl, R5 is hydrogen, n is 0, and the salts of these compounds.

Exemplary compounds according to the invention are listed in the following tables:

TABLE 1

Compounds of the formula I with R4 = 3-pyridyl, 4-pyridyl, 3-carboxyphenyl, 6-carboxypyrid-4-yl or 6-ethoxy-carbonylpyrid-4-yl, R5 = H, n = 0 and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |

TABLE 1-continued

Compounds of the formula I with R4 = 3-pyridyl, 4-pyridyl, 3-carboxyphenyl, 6-carboxypyrid-4-yl or 6-ethoxy-carbonylpyrid-4-yl, R5 = H, n = 0 and the following further substituent meanings:

| R1 | R2 | R3 |
|---|---|---|
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2-O-CH_2$ |
| $OC_2H_5$ | | $CH_2-O-CH_2$ |
| $OCH_2C_3H_5$ | | $CH_2-O-CH_2$ |
| $OCF_2H$ | | $CH_2-O-CH_2$ |
| $OCF_3$ | | $CH_2-O-CH_2$ |
| $OCH_2CF_3$ | | $CH_2-O-CH_2$ |
| $OCH_3$ | | $CH_2CH_2-O$ |
| $OC_2H_5$ | | $CH_2CH_2-O$ |
| $OCH_2C_3H_5$ | | $CH_2CH_2-O$ |
| $OCF_2H$ | | $CH_2CH_2-O$ |
| $OCF_3$ | | $CH_2CH_2-O$ |
| $OCH_2CF_3$ | | $CH_2CH_2-O$ |
| $OCH_3$ | | $CH_2CH_2-O-CH_2$ |
| $OC_2H_5$ | | $CH_2CH_2-O-CH_2$ |
| $OCH_2C_3H_5$ | | $CH_2CH_2-O-CH_2$ |
| $OCF_2H$ | | $CH_2CH_2-O-CH_2$ |
| $OCF_3$ | | $CH_2CH_2-O-CH_2$ |
| $OCH_2CF_3$ | | $CH_2CH_2-O-CH_2$ |

TABLE 2

Compounds of the formula I with R4 = 3-pyridyl, 4-pyridyl, 3-carboxyphenyl, 6-carboxypyrid-4-yl or 6-ethoxy-carbonylpyrid-4-yl, R5 = H, n = 1 and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2-O-CH_2$ |
| $OC_2H_5$ | | $CH_2-O-CH_2$ |
| $OCH_2C_3H_5$ | | $CH_2-O-CH_2$ |
| $OCF_2H$ | | $CH_2-O-CH_2$ |
| $OCF_3$ | | $CH_2-O-CH_2$ |
| $OCH_2CF_3$ | | $CH_2-O-CH_2$ |
| $OCH_3$ | | $CH_2CH_2-O$ |
| $OC_2H_5$ | | $CH_2CH_2-O$ |
| $OCH_2C_3H_5$ | | $CH_2CH_2-O$ |
| $OCF_2H$ | | $CH_2CH_2-O$ |
| $OCF_3$ | | $CH_2CH_2-O$ |
| $OCH_2CF_3$ | | $CH_2CH_2-O$ |
| $OCH_3$ | | $CH_2CH_2-O-CH_2$ |
| $OC_2H_5$ | | $CH_2CH_2-O-CH_2$ |
| $OCH_2C_3H_5$ | | $CH_2CH_2-O-CH_2$ |
| $OCF_2H$ | | $CH_2CH_2-O-CH_2$ |
| $OCF_3$ | | $CH_2CH_2-O-CH_2$ |
| $OCH_2CF_3$ | | $CH_2CH_2-O-CH_2$ |

The compounds of the formula I—if the substituents —R2 and —CH$_2$R3 are not identical—are chiral compounds. The invention therefore comprises both the pure enantiomers and their mixtures in any mixing ratio, including the racemates. The enantiomers can be separated in a manner known per se (for example by preparation and separation of corresponding diastereoisomeric compounds). Compounds of the formula I having identical substituents —R2 and —CH$_2$R3 are preferred.

The invention further relates to a process for the preparation of the compounds of the formula I and their salts. The process comprises reacting compounds of the formula II (see attached formula sheet I), in which R1, R2, R3 and R5 have the meanings indicated above and Y is a suitable leaving group, with compounds of the formula III (see attached formula sheet I), in which R4 and n have the meanings indicated above and Z is the group —C(S)—NH$_2$, and, if desired, then converting compounds of the formula I obtained into their salts or, if desired, then converting salts of the compounds of the formula I obtained into the free compounds.

The person skilled in the art is familiar on the basis of his/her expert knowledge with which leaving groups Y are suitable. For example, suitable compounds of the formula II are used as starting materials in which Y has the meaning halogen, in particular bromine or chlorine. Otherwise, the reaction is carried out in a manner familiar per se to the person skilled in the art (e.g. as described in EP 0 513 387 and EP 0 600 092) in a suitable solvent and in the presence or absence of a base, preferably at reaction temperatures between room temperature and the boiling temperature of the solvent used and with reaction times between one hour and two days. Suitable solvents are, for example, alcohols such as methanol, ethanol or propanol, cyclic hydrocarbons such as toluene or xylene, ethers such as diethyl ether, tetrahydrofuran or dioxane, halogenated hydrocarbons such as dichloromethane or chloroform, polar solvents such as dimethylformamide, acetonitrile or di-methyl sulfoxide or, if desired, also mixtures of the solvents mentioned. Preferred bases which are used are nitrogen bases such as triethylamine, ethyldiisopropylamine, N-methylmorpholine or pyridine. The bases can be added here in an equimolar ratio (based on compounds of the formula III) or preferably in an excess.

If desired, compounds of the formula I obtained can also be converted into other compounds of the formula I by use of methods known to the person skilled in the art. By way of example, the preparation of carboxamides of the formula I from the corresponding carboxylic acids of the formula I may be mentioned. To this end, the carboxylic acids of the formula I can be reacted with suitable amines in a manner such as is known to the person skilled in the art for the synthesis of carboxamides. If desired, the carboxylic acid of the formula I is converted into a suitably activated derivative, for example an appropriate acid halide, before the aminolysis. Ammonia, methylamine or ethylamine, for example, may be mentioned as suitable amines which can be employed.

By way of example, the preparation of carboxylic acids of the formula I from corresponding esters of the formula I may also be mentioned, for example by hydrolysis in a manner known to the person skilled in the art, for example as described in the examples.

If desired, quinolines, isoquinolines, pyrimidines, pyrazines, imidazoles, quinoxalines, quinazolines, benzimidazoles and in particular pyridines of the formula I obtained can also be converted into the corresponding N-oxides or their salts.

N-oxidation is carried out in a manner also familiar to the person skilled in the art, e.g. with the aid of m-chloroperoxybenzoic acid in dichloromethane at room temperature. The person skilled in the art is familiar on the basis of his/her expert knowledge with the reaction conditions which are especially necessary for carrying out the process.

The substances according to the invention are isolated and purified in a manner known per se, e.g. by distilling off the solvent in vacuo and recrystallizing the residue obtained from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating with a nonsolvent for the addition salt or by evaporation of the solvent. Salts obtained can be converted by alkalization or by acidification into the free compounds, which in turn can be converted into salts. In this way, pharmacologically intolerable salts can be converted into pharmacologically tolerable salts.

The compounds of the formula II in which R1, R2, R3 and R5 have the meanings indicated above and Y is halogen, in particular chlorine or bromine, can be obtained in a known manner, for example by chlorination or bromination of corresponding compounds of the formula II in which Y has the meaning hydrogen.

The compounds of the formula II in which R1, R2 and R3 have the meanings indicated above and R5 and Y are hydrogen, can be prepared by reaction of compounds of the formula IV (see attached formula sheet I), in which R1, R2 and R3 have the meanings indicated above and A is a nitrile group (—CN), with compounds of the formula $CH_3$—Mg—X in which X is halogen, in particular chlorine or bromine.

Compounds of the formula $CH_3$—Mg—X in which X is halogen, in particular chlorine or bromine, are accessible from the corresponding compounds of the formula $CH_3$—X by reaction with magnesium in a manner familiar to the person skilled in the art.

Alternatively, compounds of the formula II in which R1, R2 and R3 have the meanings indicated above, R5 is hydrogen and Y is halogen, in particular chlorine or bromine, can be obtained by reaction of compounds of the formula IV in which R1, R2 and R3 have the meanings indicated above and A is an activated carboxylic acid derivative, for example a carboxylic acid halide, in particular carbonyl chloride [—C(O)Cl] or carbonyl bromide [—C(O)Br], with diazomethane and subsequent treatment with HCl or with HBr. The reactions are otherwise carried out in a manner known per se to the person skilled in the art.

The compounds of the formula III in which R4 and n have the meanings indicated above and Z is the group —C(S)—$NH_2$ are either known (e.g. from EP 0 513 387 or EP 0 600 092) or can be prepared in a manner which is analogous or otherwise known to the person skilled in the art, for example by addition of hydrogen sulfide to appropriate compounds of the formula III in which Z is cyano (—CN) [W. Christ, D. Rakow, S. Strauss, J. Heterocycl. Chem. 11, 397 (1974)].

The corresponding compounds of the formula III in which Z is cyano can be prepared as described in the literature [e.g. analogously to T. Savaie, T. Ishiguro, K. Kawashima, K. Morita; Tetrahedron Lett. 1973, 2121–2124] from the corresponding compounds of the formula III in which Z is carbamoyl [—C(O)—$NH_2$].

The compounds of the formula IV in which R1, R2 and R3 have the abovementioned meanings and A is a nitrile group can be prepared as in the following examples or as described in the literature (T. Savaie, T. Ishiguro, K. Kawashima, K. Morita; Tetrahedron Lett. 1973, 2121–2124) from the corresponding compounds of the formula IV in which A has the meaning carbamoyl [—C(O)—$NH_2$].

The compounds of the formula IV in which A has the meaning carbamoyl can be prepared from the compounds of the formula IV in which A has the meaning carboxyl in a manner familiar to the person skilled in the art, for example as described in the following examples.

The compounds of the formula IV in which R1, R2 and R3 have the meanings indicated above and A is a carboxylic acid halide, in particular carbonyl chloride [—C (O)Cl], can be prepared from the compounds of the formula IV in which A has the meaning carboxyl in a manner familiar to the person skilled in the art, for example as described in the following examples.

A further variant for the preparation of compounds of the formula II in which R1, R2, R3 and R5 have the meanings indicated above and Y is hydrogen is the reaction of compounds of the formula IV, in which R1, R2 and R3 have the meanings indicated above and A is lithium, with compounds of the formula R5—$CH_2$—C(O)W in which R5 has the meaning indicated above and W is a suitable leaving group. Particularly suitable leaving groups W are, for example, halogens, in particular chlorine or bromine or alternatively 1–4C-alkoxy radicals.

Compounds of the formula IV in which R1, R2 and R3 have the meanings indicated above and A is lithium can be obtained from corresponding compounds of the formula IV in which A is halogen, in particular bromine, by reaction with an alkyllithium compound, for example butyllithium, under customary reaction conditions.

Compounds of the formula IV in which R1, R2 and R3 have the meanings indicated above and A has the meaning carboxyl are either known from the international patent application WO96/03399 or can be prepared in an analogous manner.

Compounds of the formula IV in which R1, R2 and R3 have 15 the meanings indicated above and A is halogen, in particular bromine, can be prepared from known precursors according to the general reaction scheme on the attached formula sheet II. The synthesis of corresponding compounds of the formula IV is described by way of example under starting compounds. Further compounds of the formula IV can be prepared in an analogous manner.

Compounds of the formula R5—CH$_2$—C(O)W in which R5 has the meaning indicated above and W is a suitable leaving group are either known or can be obtained in a manner known per se to the person skilled in the art from the corresponding compounds of the formula R5—CH$_2$—C(O)W in which W is hydroxyl.

The following examples illustrate the invention in greater detail, without restricting it. Further compounds of the formula I, whose preparation is not described explicitly, can also be prepared in an analogous manner or in a manner familiar per se to the person skilled in the art using customary process techniques.

In the examples, m.p. stands for melting point, h for hour(s), RT for room temperature, min. for minute(s), THF for tetrahydrofuran, DMF for dimethylformamide, tol. for toluene, EA for ethyl acetate, TLC for thin-layer chromatography and PE for petroleum ether. The compounds mentioned in the examples and their salts are a preferred subject of the invention.

EXAMPLES

Final Products

3-[4-(2,3-Dihydro-7-methoxybenzofuran-2-spiro-1'-cyclopentan-4-yl) thiazol-2-yl]pyridine 488 mg (1.5 mmol) of 2-bromo-1-(2,3-dihydro-7-methoxybenzofuran-2-spiro-1'-cyclopentan-4-yl)ethanone and 250 mg (1.7 mmol) of thionicotinamide are stirred at RT for 16 h in 10 ml of ethanol. The suspension obtained is partitioned between 100 ml of ethyl acetate and 100 ml of 2 N NaOH, the phases are separated and the organic phase is washed with 100 ml of saturated sodium chloride solution. The organic phase is dried over MgSO$_4$ and evaporated, and the residue is recrystallized from 5 ml of 80% strength ethanol. 290 mg (53%) of the title compound of m.p. 120–122° C. are obtained.

2. 4-[4-(2,3-Dihydro-7-methoxybenzofuran-2-spiro-1'-cyclopentan-4-yl)thiazol-2-yl]pyridine 439 mg (1.35 mmol) of 2-bromo-1-(2,3-dihydro-7-methoxybenzofuran-2-spiro-1'-cyclopentan-4-yl)ethanone and 221 mg (1.6 mmol) of thioisonicotinoyl chloride are stirred at RT for 20 h in 10 ml of ethanol. The reaction mixture is partitioned between 50 ml of ethyl acetate and 50 ml of 2 N NaOH, the phases are separated and the organic phase is washed with 50 ml of water and 50 ml of saturated sodium chloride solution. The organic phase is dried over MgSO$_4$ and evaporated, and the resinous residue is crystallized from 5 ml of ethanol. 172 mg (35%) of the title compound of m.p. 127–129° C. are obtained.

3. Ethyl 4-[4-(2,3-Dihydro-7-methoxybenzofuran-2-spiro-1'-cyclopentan-4-yl)thiazol-2-yl]pyridine-2-carboxylate 488 mg (1.5 mmol) of 2-bromo-1-(2,3-dihydro-7-methoxybenzofuran-2-spiro-1'-cyclopentan-4-yl)ethanone and 315 mg (1.5 mmol) of ethyl 4-thioamidopyridine-2-carboxylate are reacted analogously to compound 2. After a reaction time of 24 h, 280 mg (41%) of the title compound of m.p. 145–147° C. are obtained.

4. 4-[4-(2,3-Dihydro-7-methoxybenzofuran-2-spiro-1'-cyclopentan-4-yl)thiazol-2-yl]pyridine-2-carboxylic acid semihydrochloride 136 mg (0.3 mmol) of the compound 3 and 28.7 mg (1.2 mmol) of lithium hydroxide are suspended in a mixture of 10 ml of methanol and 10 ml of water. After stirring at RT for 4 h, the reaction solution, which has meanwhile become clear, is concentrated. The residue is dissolved in 5 ml of ethanol, acidified to pH=0–1 using 6 N HCl and the title compound is crystallized by addition of 4 ml of water. The crystals are filtered off and dried and 90 mg (69%) of the title compound of m.p. 220° C. (decomposition) are obtained.

5. 3-[4-(2,3-Dihydro-7-methoxybenzofuran-2-spiro-1'-cyclopentan-4-yl)thiazol-2-yl]benzoic acid 975 mg (3.0 mmol) of 2-bromo-1-(2,3-dihydro-7-methoxybenzofuran-2-spiro-1'-cyclopentan-4-yl)ethanone and 725 mg (4.0 mmol) of 3-thioamidobenzoic acid are stirred at RT for 3 days with addition of 1 ml of triethylamine in 20 ml of ethanol. The mixture is concentrated and the residue is taken up in 150 ml of ethyl acetate and 150 ml of water and acidified with 1 N HCl until the reaction is acidic. The phases are separated, the aqueous phase is extracted twice with 50 ml of ethyl acetate each time and the combined organic phases are washed with 100 ml of saturated NaCl solution. The organic phase is concentrated and chromatographed on silica gel (tol/AcOH=50:1). The product-containing fractions are concentrated and the residue is crystallized from 50% strength ethanol. The title compound of m.p. 215–217° C. is obtained.

Starting Compounds

A. 2-Bromo-1-(2,3-dihydro-7-methoxybenzofuran-2-spiro-1'-cyclopentan-4-yl)ethanone 2.8 ml (54 mmol) of bromine are added dropwise with ice-cooling to a solution of 11.0 g (45 mmol) of 1-(2,3-dihydro-7-methoxybenzofuran-2-spiro-1'-cyclopentan-4-yl) ethanone in 160 ml of methanol. The mixture is then stirred for 1 h. The reaction solution is treated with 200 ml of ethyl acetate and extracted by shaking with 200 ml of water. The organic phase is separated off, washed first with saturated bicarbonate solution, then with saturated NaCl solution, dried over magnesium sulfate and concentrated. The resinous residue is chromatographed on silica gel (tol/EA=20:1), the productcontaining fractions are concentrated and the residue is recrystallized from 80 ml of petroleum ether. 6.4 g (44%) of the title compound of m.p. 73–75° C. are obtained.

B. 1-(2,3-Dihydro-7-methoxybenzofuran-2-spiro-1'-cyclopentan-4-yl)ethanone 25 ml (75 mmol) of a 20% strength solution of methylmagnesium chloride in THF are added at RT to a solution of 10.7 g (47.0 mmol) of 4-cyano-2,3-dihydro-7-methoxybenzofuran-2-spiro-1'-cyclopentane in 100 ml of THF. The mixture is then heated to reflux for 7 h. It is then cautiously hydrolyzed with 20 ml of water, treated with 50 ml of half-concentrated sulfuric acid and heated to reflux for 90 min. The phases are separated, the aqueous phase is extracted with 2×70 ml of ethyl acetate, and the combined organic phases are again washed with 100 ml of water, 100 ml of saturated sodium bicarbonate solution and 100 ml of saturated NaCl solution. The organic phase is dried over magnesium sulfate, concentrated and 11.0 g (96%) of the title compound are obtained, which is employed without further purification for the synthesis of compound A.

C. 4-Cyano-2,3-dihydro-7-methoxybenzofuran-2-spiro-1'-cyclopentane 1.4 g (6.0 mmol) of 2,3-dihydro-7-methoxybenzofuran-2-spiro-1'-cyclopentanecarboxamide are dissolved in 25 ml of CHCl$_3$ and treated with 210 mg (1.0 mmol) of benzyltriethylammonium chloride. 5 ml of 50% strength NaOH are added with ice-cooling and the mixture is stirred at 15° C. for 3 h. It is treated with H$_2$O, extracted with ethyl acetate and chromatographed on silica gel (tol.). Crystallization is carried out from 5 ml of petroleum ether and 998 mg (77%) of the title compound of m.p. 74–76° C. are obtained.

D. 2,3-Dihydro-7-methoxybenzofuran-3-spiro-1'-cyclopentan-4-ylcarboxamide 3.5 g (14.0 mmol) of 2,3-dihydro-7-methoxybenzofuran-2-spiro-1'-cyclopentan-4-ylcarboxylic acid are treated with 10 ml (about 140 mmol) of $SOCl_2$. The excess $SOCl_2$ is distilled off in vacuo and the residue is taken up in 20 ml of acetone. The mixture is treated with 10 ml of conc. $NH_3$ with ice-cooling and stirred for 1 h. The acetone is distilled off and the residue is partitioned between ethyl acetate and 0.5 N NaOH. The dried organic phase is crystallized from 5 ml of 50% strength methanol and 115 mg (48%) of the title compound of m.p. 149–151° C. are obtained.

E. 2,3-Dihydro-7-methoxybenzofuran-2-spiro-1'-cyclopentan-4-ylcarboxamide

The preparation of the title compound is described in the international patent application WO96/03399.

F. 1-(2,3-Dihydro-7-methoxybenzofuran-2-spiro-1'-cyclopentan-4-yl)ethanone 17 ml (27 mmol) of a 1.6 N solution of butyllithium in heptane are added dropwise at −50° C. to a solution of 6.36 g (22.5 mmol) of 4-bromo-2,3-dihydro-7-methoxybenzofuran-2-spiro-1'-cyclopentane in 125 ml of diethyl ether. The reaction mixture is then stirred at 0° C. for 30 min., treated with 10 ml of ethyl acetate at −60° C. and allowed to come to RT. It is hydrolyzed at −20° C., then the aqueous phase is extracted with 50 ml of ethyl acetate, the combined organic phases are dried over magnesium sulfate and concentrated and the residue is chromatographed on silica gel (tol/EA=50:1). The product-containing fractions are evaporated and the title compound is obtained as a colorless oil.

G. 4-Bromo-2,3-dihydro-7-methoxybenzofuran-2-spiro-1'-cyclopentane 9.0 g of Amberlyst 15 are added to a solution of 8.4 g (0.03 mol) of the compound prepared according to H. in 100 ml of absolute toluene and the mixture is stirred at 100° C. for 10 h. After cooling the mixture, the $H^+$ ion exchanger is filtered off and washed with 100 ml of methanol. After stripping off the organic phase and column chromatography, 7.4 g (88% of theory) of the title compound are obtained as a yellow oil. [TLC (PE/ethyl ether, 6:4) $R_f$=0.72].

H. 4-Cyclopent-1-enylmethyl-3-hydroxy-4-methoxybromobenzene 52.1 ml (0.082 mol) of n-butyllithium are added dropwise at −78° C. under nitrogen to a suspension of 26.5 g (0.074 mol) of methyltriphenylphosphonium bromide in 200 ml of absolute THF. The suspension is then warmed to −30° C., the suspension going into solution. After fresh cooling to −70° C., a solution of 19.2 g (0.067 mol) of the compound prepared according to I. is added dropwise under nitrogen in 200 ml of absolute THF. The mixture is then warmed to −10° C. and stirred at this temperature for 5 h. [TLC (PE/ethyl ether, 6:4) $R_f$ (methylene compound)=0.81]. After warming to RT, solids are filtered off from the mixture, and the filtrate is extracted by shaking with 3×200 ml of half-saturated sodium chloride solution and 2×200 ml of distilled water. After combining the organic phases, drying over sodium sulfate and concentrating to dryness, the residue is taken up in 50 ml of quinoline and stirred at 195–205° C. for 1 h. After cooling the solution, 400 ml of ethyl ether are added and the quinoline is extracted by shaking with 4×200 ml of 2N hydrochloric acid. The organic phases are combined, dried over sodium sulfate and concentrated. After column chromatography, a yield of 8.4 g (44% of theory) of the title compound as a red-brown oil results. [TLC (PE/ethyl ether, 6:4) $R_f$=0. 65].

I. Methoxy-3-(2-oxocyclopentyloxy)bromobenzene 17.7 g (0.15 mol) of 2-chlorocyclopentanone and 41.4 g (0.3 mol) of potassium carbonate are added to a solution of 20 g (0.1 mol) of 3-hydroxy-4-methoxybromobenzene in 300 ml of absolute DMF and the mixture is stirred at RT for 12 h. After filtering off the solids, the filtrate is concentrated, the residue is taken up in 500 of ethyl ether and the mixture is extracted by shaking with 3×200 ml of distilled water. Column chromatography affords 21.1 g (75% of theory) of the title compound as a brown oil [TLC (PE/ethyl ether, 6:4) $R_f$=0.47].

J. Ethyl 4-cyanopyridine-2-carboxylate

A solution of 1.88 g (10.6 mmol) of ethyl 4-cyanopyridine-2-carboxylate in 10 ml of pyridine and 2 ml of triethylamine is saturated with hydrogen sulfide. After 16 h at RT, the mixture is concentrated, the residue is taken up in 100 ml of ethyl acetate and the mixture is washed first with 100 ml of saturated sodium bicarbonate solution, then with 100 ml of water. The organic phase is dried over magnesium sulfate and concentrated, and the residue is recrystallized from 20 ml of ethanol. 1.92 g (86%) of the title compound of m.p. 170–172° C. are obtained.

K. Ethyl 4-cyanopyridine-2-carboxylate

The preparation of the compound is known from the literature. Ref.: G. Heinisch, G. Lötsch; Angew. Chem. 97, 694 (1985).

L. 3-Thiocarbamoylbenzoic acid

The preparation of the compound is known from the literature. Ref.: Science Union, German patent 21 29 090 (1971); CA 76, 85810 (1972).

Commercial Utility

The compounds according to the invention have valuable pharmacological properties which make them commercially utilizable. As selective cyclic nucleotide phosphodiesterase (PDE) inhibitors (namely of type IV), they are suitable on the one hand as bronchial therapeutics (for the treatment of airway obstructions on account of their dilating but also on account of their respiratory rate- or respiratory drive-increasing action) and for the elimination of erectile dysfunction on account of the vasodilatory action, but on the other hand especially for the treatment of disorders, in particular of inflammatory nature, e.g. of the airways (asthma prophylaxis), of the skin, of the intestine, of the eyes and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen radicals and proteases. The compounds according to the invention are distinguished here by a low toxicity, a good enteral absorption (high bioavailability), a great therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and llergen-induced) airway disorders of various origins (bronchitis, allergic bronchitis, bronchial asthma); dermatoses (especially of proliferative, inflammatory and allergic type) such as, for example, psoriasis (vulgaris), toxic and allergic contact eczema, atopic eczema, seborrheic eczema, lichen simplex, sunburn, pruritis in the anogenital area, alopecia areata, hypertrophic scars, discoid lupus erythematosus, follicular and wide-area pyodermias, endogenous and exogenous acne, acne rosacea and other proliferative, inflammatory and allergic skin disorders; disorders which are based on an excessive release of TNF and leukotrienes, for instance disorders of the arthritis type (rheumatoid arthritis, rheumatoid spondylitis, osteoarthritis and other arthritic conditions), disorders of the immune system (AIDS, multiple sclerosis), symptoms of shock [septic shock, endotoxin shock, gram-negative sepsis, toxic shock syndrome and ARDS (adult respiratory distress syndrome)] and generalized inflammations in the gastrointestinal region (Crohn's disease and ulcerative colitis); disorders which are based on allergic and/or chronic, faulty immunological reactions in the area of the upper airways (pharynx, nose) and the adjoining regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and the ureters in connection with kidney stones; or alternatively disorders of the CNS, such as, for example, depression or arteriosclerotic dementia.

A further subject of the invention is a process for the treatment of mammals, including humans, which are suffering from one of the abovementioned illnesses. The process comprises administering to the sick mammal a therapeutically efficacious and pharmacologically tolerable amount of one or more of the compounds according to the invention.

A further subject of the invention are the compounds, according to the invention for use in the treatment and/or prophylaxis of the illnesses mentioned.

The invention also relates to the use of the compounds according to the invention for the production of medicaments which are employed for the treatment and/or prophylaxis of the illnesses mentioned.

Pharmaceuticals for the treatment and/or prophylaxis of the illnesses mentioned and which contain one or more of the compounds according to the invention are fur-thermore a subject of the invention.

The medicaments are produced by processes which are known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar, on the basis of his/her expert knowledge, with the auxiliaries which are suitable for the desired pharmaceutical formulations. In addition to solvents, gel-forming agents, bases and other active compound carriers, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this, these are either administered directly as a powder (preferably in micronized form) or by nebulization of solutions or suspensions which contain them. With respect to the preparations and administration forms, reference is made, for example, to the details in European patent 163 965.

For the treatment of dermatoses, the administration of the compounds according to the invention is in particular carried out in the form of those medicaments which are suitable for topical application. For the production of the medicaments, the compounds according to the invention (=active compounds) are preferably mixed with suitable pharmaceutical auxiliaries and processed further to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are produced by processes known per se. The dosage of the active compounds takes place in the customary order of magnitude for PDE inhibitors. Thus topical application forms (such as, for example, ointments) for the treatment of dermatoses contain the active compounds in a concentration of, for example, 0.1–99%. The dose for administration by inhalation is customarily between 0.01 and 1 mg per burst of spray. The customary dose in the case of systemic therapy p.o. or i.v. is between 0.1 and 200 mg per administration.

Biological Investigations

In the investigation of PDE IV inhibition at the cellular level, the activation of inflammatory cells is ascribed particular importance. As an example, the FMLP (N-formyl-methionyl-leucyl-phenylalanine)-induced superoxide production of neutrophilic granulocytes may be mentioned, which can be measured as luminol-potentiated chemoluminescence. [McPhail LC, Strum SL, Leone PA and Sozzani S, The neutrophil respiratory burst mechanism. In "Immunology Series" 57: 47–76, 1992; ed. Coffey RG (Marcel Decker, Inc., New York-Basel-Hong Kong)].

Substances which inhibit chemoluminescence and cytokine secretion and the secretion of proinflammatory mediators from inflammatory cells, in particular neutrophilic and eosinophilic granulocytes, are those which inhibit PDE IV. This isoenzyme of the phosphodiesterase families is particularly represented in granulocytes. Its inhibition leads to an increase in the intracellular cyclic AMP concentration and thus to the inhibition of cellular activation. The PDE IV inhibition by the substances according to the invention is thus a central indicator of the suppression of inflammatory processes. (Giembycz MA, Could isoenzyme-selective phosphodiesterase inhibitors render bronchodilatory therapy redundant in the treatment of bronchial asthma? Biochem Pharmacol 43: 2041–2051, 1992; Torphy TJ et al., Phosphodiesterase inhibitors: new opportunities for treatment of asthma. Thorax 46: 512–523, 1991; Schudt C et al., Zardaverine: a cyclic AMP PDE III/IV inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and $Ca_i$. Naunyn-Schmiedebergs Arch Pharmacol 344: 682–690, 1991; Nielson CP et al., Effects of selective phosphodiesterase inhibitors on polymorphonuclear leukocyte respiratory burst. J Allergy Clin Immunol 86: 801–808, 1990; Schade et al., The specific type III and IV phosphodiesterase inhibitor zardaverine suppress formation of tumor necrosis factor by macrophages. European Journal of Pharmacology 230: 9–14, 1993).

INHIBITION OF PDE IV ACTIVITY

Methodology

The activity test was carried out according to the method of Bauer and Schwabe, which was adapted to microtiter plates (Naunyn-Schmiedeberg's Arch. Pharmacol. 311, 193–198, 1980). In this test, the PDE reaction takes place in the first step. In a second step, the charged 5'-nucleotide is cleaved to give the uncharge nucleoside by a 5'-nucleotidase of the snake veno of Ophiophagus hannah (king cobra). In the third step, the nucleoside is separated from the remaining charged substrate on ion exchange columns. The columns are eluted directly into minivials using 2 ml of 30 mM ammonium formate (pH 6.0) to which a further 2 ml of scintillator fluid is added for counting.

The inhibitory values determined for the compounds according to the invention result from Table 1 which follows, in which the numbers of the compounds correspond to the numbers of the examples.

TABLE 1

| Inhibition of PDE IV activity | |
| --- | --- |
| Compound | $-\log IC_{50}$ |
| 1 | 7.74 |
| 2 | 7.25 |
| 3 | 7.22 |
| 4 | 6.85 |
| 5 | 7.79 |

We claim:
1. A compound of formula I

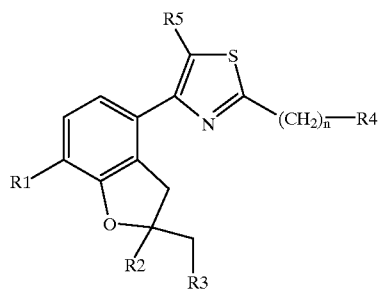

(I)

in which
R1 is hydroxyl, 1–4C-alkoxy, 3–7C-cycloalkoxy, 3–7C-cycloalkylmethoxy, benzyloxy or 1–4C-alkoxy which is completely or mainly substituted by fluorine,
R2 is hydrogen or 1–4C-alkyl and
R3 is hydrogen or 1–4C-alkyl,
or
R2 and R3, together and including the two carbon atoms to which they are bonded, are a 5-, 6- or 7-membered hydrocarbon ring which, if desired, is interrupted by an oxygen atom,
R4 is a phenyl or naphthyl ring which is substituted by R41, R42 and R43, a mono- or bicyclic heterocycle which is substituted by R44, R45 and R46 and which is selected from the group consisting of pyridine, pyrrole, quinoline, isoquinoline, indole, isoindole, indolizine, pyrimidine, pyrazine, pyridazine, quinoxaline, quinazoline, cinnoline, benzimidazole, thiophene and furan or a mono- or bicyclic heterocycle which is substituted by R44 and R45 and which is selected from the group consisting of pyrazole, imidazole, purine, oxazole, isoxazole, thiazole and isothiazole, where
R41 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylami-nosulfonyl, amino, mono- or di-1–4C-alkylamino, 1–4C-alkylcarbonylamino, 1–4C-alkylsulfonyl, 1–4C-alkoxysulfonyl, hydroxy-1–4C-alkyl, hydroxyl, 1–4C-alkoxy, 1–4C-alkyl, 1–4C-alkylcarbonyl, 1–4C-alkylcarbonyloxy, halogen, cyano or nitro,
R42 is hydrogen, 1–4C-alkoxy which is completely or mainly substituted by fluorine, hydroxyl, amino, nitro, halogen, 1–4C-alkoxycarbonyl, 1–4C-alkylcarbonyloxy, 1–4C-alkylcarbonyl, carboxyl, 1–4C-alkyl or 1–4C-alkoxy,
R43 is hydrogen, 1–4C-alkoxy, halogen or hydroxyl,
R44 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, hydroxy-1–4C-alkyl, hydroxyl, 1–4C-alkoxy, 1–4C-alkyl, 1–4C-alkylcarbonyl, 1–4C-alkylcarbonyloxy, halogen, cyano or nitro,
R45 is hydrogen, hydroxyl, halogen, carboxyl, amino, 1–4C-alkyl, 1–4C-alkylcarbonyl, 1–4C-alkoxycarbonyl or 1–4C-alkoxy and
R46 is hydrogen, halogen, 1–4C-alkoxy or 1–4C-alkyl,
R5 is hydrogen or halogen,
n is 0, 1 or 2,
a salt of this compound or a N-oxides of a pyridine, quinoline, isoquinoline, pyrimidine, pyrazine, imidazole, quinoxaline, quinazoline or benzimidazole or a salt.
2. A compound of formula I as claimed in claim 1, in which
R1 is 1–4C-alkoxy, 3–5C-cycloalkoxy, 3–5C-cycloalkylmethoxy or 1–4C-alkoxy which is completely or mainly substituted by fluorine,
R2 is 1–4C-alkyl and
R3 is hydrogen or 1–4C-alkyl,
or
R2 and R3, together and including the two carbon atoms to which they are bonded, are a cyclopentane, cyclohexane, tetrahydrofuran or tetrahydropyran ring,
R4 is a phenyl ring which is substituted by R41 and R42 or a mono- or bicyclic heterocycle which is substituted by R44 and R45 and which is selected from the group consisting of pyridine, pyrrole, quinoline, isoquinoline, indole, isoindole, indolizine, pyrimidine, pyrazine, pyridazine, pyrazole, imidazole, quinoxaline, quinazoline, cinnoline, benzimidazole, oxazole, isoxazole, thiazole and isothiazole, where
R41 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, 1–4C-alkylsulfonyl, 1–4C-alkoxysulfonyl, hydroxy-1–4C-alkyl, hydroxyl, 1–4C-alkoxy, 1–4C-alkyl, 1–4C-alkylcarbonyl, 1–4C-alkylcarbonyloxy, halogen, cyano or nitro,
R42 is hydrogen, hydroxyl, nitro, halogen, 1–4C-alkoxycarbonyl, 1–4C-alkylcarbonyloxy, 1–4C-alkylcarbonyl, carboxyl, or 1–4C-alkoxy,
R44 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C- alkylamino, 1–4C-alkylcarbonylamino, hydroxy-1–4C-alkyl, hydroxyl, 1–4C-alkoxy, 1–4C-alkyl, 1–4C-alkylcarbonyl, halogen or cyano and R45 is hydrogen, hydroxyl, halogen, carboxyl, amino, 1–4C-alkyl, or 1–4C-alkoxy, R5 is hydrogen or halogen, n is 0 or 1, a salt of this compound or an N-oxide of a pyridine, quinoline, isoquinoline, pyrimidine, imidazole, quinoxaline, quinazoline or benzimidazole or a salt thereof.

3. A compound of formula I as claimed in claim 1, in which

R1 is 1–4C-alkoxy, 3–5C-cycloalkoxy or 1–2C-alkoxy which is completely or mainly substituted by fluorine, R2 and R3, together and including the two carbon atoms to which they are bonded, are a cyclopentane or cyclohexane ring, R4 is a phenyl ring which is substituted by R41 and R42 or a mono- or bicyclic heterocycle which is substituted by R44 and R45 and which is selected from the group consisting of pyridine, pyrrole, quinoline, isoquinoline, indole, isoindole, indolizine and pyrazine, where R41 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, 1–4C-alkylsulfonyl, 1–4C-alkoxysulfonyl, hydroxy-1–4C-alkyl, hydroxyl, 1–4C-alkoxy, 1–4C-alkyl, 1–4C-alkylcarbonyl, 1–4C-alkylcarbonyloxy, halogen, cyano or nitro, R42 is hydrogen, hydroxyl, nitro, halogen, 1–4C-alkoxycarbonyl, 1–4C-alkylcarbonyloxy, 1–4C-alkylcarbonyl, carboxyl or 1–4C-alkoxy, R44 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, hydroxy-1–4C-alkyl, hydroxyl, 1–4C-alkoxy, 1–4C-alkyl, 1–4C-alkylcarbonyl, halogen or cyano and R45 is hydrogen, hydroxyl, halogen, carboxyl, amino, 1–4C-alkyl or 1–4C-alkoxy, R5 is hydrogen, n is 0, a salt of this compound or an N-oxide of the pyridine, quinoline or isoquinoline or a salt thereof.

4. A compound of formula I as claimed in claim 1, n which

R1 is 1–4C-alkoxy or 1–2C-alkoxy which is completely or mainly substituted by fluorine, R2 and R3, together and including the two carbon atoms to which they are bonded, are a cyclopentane ring, R4 is a phenyl ring which is substituted by R41 and R42 or pyridine or pyrazine which is substituted by R44 and R45, where R41 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, 1–4C-alkylsulfonyl, 1–4C-alkoxysulfonyl, hydroxy-1–4C-alkyl, hydroxyl, 1–4C-alkoxy, 1–4C-alkyl, 1–4C-alkylcarbonyl, 1–4C-alkylcarbonyloxy, halogen, cyano or nitro, R42 is hydrogen, hydroxyl, nitro, halogen, 1–4C-alkoxycarbonyl, 1–4C-alkylcarbonyloxy, 1–4C-alkylcarbonyl, carboxyl or 1–4C-alkoxy, R44 is hydrogen, carboxyl, 1–4C-alkoxycarbonyl, carbamoyl, hydroxysulfonyl, sulfamoyl, mono- or di-1–4C-alkylaminocarbonyl, mono- or di-1–4C-alkylaminosulfonyl, amino, mono- or di-1–4C-alkylamino, 1–4C-alkylcarbonylamino, hydroxy-1–4C-alkyl, hydroxyl, 1–4C-alkoxy, 1–4C-alkyl, 1–4C-alkylcarbonyl, halogen or cyano and R45 is hydrogen, hydroxyl, halogen, carboxyl, amino, 1–4C-alkyl or 1–4C-alkoxy, R5 is hydrogen, n is 0, a salt of this compound or an N-oxide of a pyridine or a salt thereof.

5. A compound of formula I as claimed in claim 1, in which

R1 is 1–4C-alkoxy,

R2 and R3, together and including the two carbon atoms to which they are bonded, are a cyclopentane ring, R4 is a phenyl ring which is substituted by R41 or pyridine which is substituted by R44, where R41 is hydrogen, carboxyl, 1–4C-alkoxycarbonyl, carbamoyl, hydroxysulfonyl, sulfamoyl or hydroxyl and R44 is hydrogen, carboxyl, 1–4C-alkoxycarbonyl, carbamoyl, hydroxysulfonyl, sulfamoyl or hydroxyl, R5 is hydrogen, n is 0 or a salt thereof.

6. A compound of formula I as claimed in claim 1, in which

R1 is methoxy,

R2 and R3, together and including the two carbon atoms to which they are bonded, are a cyclopentane ring, R4 is a phenyl ring which is substituted by R41 or pyridine which is substituted by R44, where R41 is carboxyl and R44 is hydrogen, carboxyl or 1–4C-alkoxycarbonyl, R5 is hydrogen, n is 0, or a salt thereof.

7. A medicament composition useful for treating an airway disorder and comprising an effective amount of a pharmacologically-acceptable compound as claimed in claim 1 and a customary pharmaceutical auxiliary and/or carrier.

8. A method of treating a subject afflicted with an amenable airway disorder which comprises administering to the subject an effective amount of a pharmacologically-acceptable compound as claimed in claim 1.

9. In a method of compounding a medicament composition by combining an active ingredient useful for treating an airway disorder with a customary pharmaceutical auxiliary and/or carrier, the improvement wherein the active ingredient is a pharmacologically-acceptable compound as claimed in claim 1.

* * * * *